United States Patent
Sardashti et al.

(10) Patent No.: US 6,204,664 B1
(45) Date of Patent: Mar. 20, 2001

(54) CHEMOMETRIC TECHNIQUE FOR PREDICTING STYRENE CONTENT IN BUTADIENE-STYRENE RESIN WITH AN ON-LINE NMR SYSTEM

(75) Inventors: Maziar Sardashti, Bartlesville, OK (US); Xiaonian Lai, Burlingame, CA (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/224,326

(22) Filed: Dec. 31, 1998

(51) Int. Cl.[7] .................................................. G01V 3/00
(52) U.S. Cl. ........................ 324/306; 324/307; 324/300
(58) Field of Search .................................. 324/306, 307, 324/300

(56) References Cited

U.S. PATENT DOCUMENTS

| | | | |
|---|---|---|---|
| 5,302,897 | 4/1994 | Tache et al. | 324/300 |
| 5,596,275 | 1/1997 | Dechene et al. | 324/307 |
| 5,675,253 | 10/1997 | Smith et al. | 324/306 |

OTHER PUBLICATIONS

Sharaf, et al., *Chemometrics*, 1986, pp. 281–292.
Beebe, et al., *Chemometrics A Practical Guide*, 1998, pp. 245–338.

Primary Examiner—Jay Patidar
Assistant Examiner—Brij B. Shrivastav
(74) Attorney, Agent, or Firm—Richmond, Hitchcock, Fish & Dollar

(57) ABSTRACT

A chemometric technique for predicting styrene content in Butadiene-Styrene resin (K-Resin) using an on-line NMR system comprising the steps of producing a predictive data set and using the predictive data set to obtain unknown concentrations of styrene in samples of K-Resin. The predictive data set is generated by obtaining free induction decays for samples of K-Resin with measured concentrations of styrene to produce a free induction decay data set; analyzing the free induction decay data set using PCA to produce a principle component data set; analyzing the styrene concentrations, the free induction decay data set and the principle component data set using PLS to produce a training data set; and validating the training data set to produce a predictive data set. Using the predictive data set involves the steps of obtaining free induction decays of samples of K-Resin with unknown concentrations of styrene and applying the free induction decays to the predictive data set to predict the unknown concentrations.

21 Claims, 1 Drawing Sheet

CHEMOMETRIC TECHNIQUE FOR PREDICTING STYRENE CONTENT IN BUTADIENE-STYRENE RESIN WITH AN ON-LINE NMR SYSTEM

FIELD OF THE INVENTION

The present invention relates generally to the field of measurement of polymer properties with a process NMR system, and more particularly to the use of chemometrics to find correlations for NMR data to predict the concentration of styrene in butadiene-styrene resin.

BACKGROUND OF THE INVENTION

In the chemical industry, it is important to effectuate precise prediction of properties of compounds. Several methods have been employed, including wet methods such as extraction. However, such methods have proven to be time consuming and yield low precision results. A typical method of determining properties has therefore been through instrumental analysis. In particular, the use of quantized energy states of matter through spectroscopy solves many of the efficiency problems involved in methods such as extraction.

Nuclear magnetic resonance (NMR) is a powerful spectroscopic technique for structural analysis which utilizes commonly found elements such as hydrogen and carbon as "chromophores." With the aid of NMR, it is possible to define the environment of practically all commonly occurring functional groups, as well as fragments (e.g., hydrogen atoms attached to carbon) that are not otherwise accessible to spectroscopic or analytical techniques.

The single most important application of NMR has been in the qualitative identification of organic compounds and the elucidation of their structure. However, NMR can also be used for quantitative determination of compounds in mixtures and hence for following the progress of chemical reactions. More sophisticated applications often yield kinetic and thermodynamic parameters for certain types of chemical processes; and others, in particular spin-spin coupling, often give accurate information about the relative positions of groups of magnetic nuclei within molecules.

One means of obtaining an NMR spectrum involves the application of a strong radio frequency (RF) pulse of energy over the whole range of frequencies while the magnetic field is kept constant. As a result, nuclei are flipped to their upper state from which, over time, they will return (decay) to the lower state. Collecting the thus-induced current as a function of time through a computer creates a time-domain signal, which is a generally complex pattern called the free-induction decay (FID). Interpretation of an FID is often difficult; however, a Fourier transformation of an FID performed on the same dedicated computer yields a spectrum virtually identical to the regular absorption spectrum. This type of spectroscopy is called Fourier transform (FT) spectroscopy and is mostly applied on "high resolution" instruments with high magnetic fields (i.e. 2–14 Tesla).

NMR instruments that are used for process purposes typically have very low magnetic fields (i.e. ~0.5 Tesla). However, at such low magnetic fields, there are not enough energy differences between different types of nuclei to resolve them by FT, especially in analyzing solid samples. Therefore, the time domain signal, or FID, is the main source of information for low magnetic field instruments. However, interpretation of the FID data when using the NMR for industrial process analysis and control can be quite difficult. Prior art methods suggest solutions that involve various iterative techniques for interpreting and thereafter utilizing the FID curve to interpret properties of compounds. Such methods involve the use of large tables of data with a single equation for interpreting the FID curve or alternatively, construction of a mathematic model where the results of experiments are expressed as a mathematical function of the experimental conditions. The mathematical function method provides a means of predicting and estimating the results at levels that were not directly studied. The mathematical equation that expresses the results (e.g., solubility of inorganic salts) in terms of the experimental factors (e.g., temperature and ionic strength) is referred to as the model. The experimental results are referred to as the responses. For optimization purposes, such a model can be very crucial.

To construct the model, instrument responses from samples with known concentration levels are measured and a mathematical relationship is estimated which relates the instrument response to the concentration of the chemical component(s). This model may be used to predict the concentration of a chemical component in future samples using the measured instrument response(s) from those samples. Prior art applications such as U.S. Pat. No. 5,675,253 issued to Smith et al. ("Smith '253") discloses developing such a mathematical model. In particular, the patent discloses using a Marquardt-Levenberg (M-L) curve-fitting approximation technique to determine the magnitude of all the parameters that best fit the FID curves. Smith '253 further teaches a calibration procedure which compares known samples and curve-fit points using time function equations including Gaussians, exponentials, Abragrams (defined herein as Gaussian multiplied by the quantity sin ($\infty$t) divided by $\infty$t), modified exponentials (defined herein as $Ce^{-z}$ where C is a constant, $z=(kt)$, and lies between 0 and 1 or 1 and 2), modified Gaussians (defined herein as Gaussian multiplied by the cosine of the square root of t), and trigonometrics. However, such a curve-fitting procedure decreases the accuracy of the model and thus the accuracy of the resulting prediction.

There is a continuing need in the industry for an improved on-line system of relating multiple responses from an instrument to a property or properties of a polymer to enhance the accuracy, precision, and efficiency of prediction.

SUMMARY OF INVENTION

The present invention provides a process of using an on-line procedure to predict properties of a polymer sample using chemometric techniques.

In a preferred embodiment, extraction is used to create a first sample set of known concentrations of styrene in samples of homo- and co-polymers of butadiene-styrene ("K-Resin"). A process low-resolution nuclear magnetic resonance spectrometer (NMR) is used to obtain the free induction decay of each of said sample to create a free induction decay data set. Each data point of the free induction decay data sets are then analyzed using principle component analysis to create latent variables, thereby creating a principle component data set. The first sample set, the free induction decay data set, and the principle component data set are analyzed using partial least squares analysis to create a predictive calibration model having a predictive data set. The predictive data set is then validated using both internal cross-validation and external validation with a second smaller data set.

An unknown sample set containing compositions of homo- and co-polymers of K-Resin are placed in the NMR instrument to obtain the free induction decay of each of said compositions of K-Resin to create a second free induction decay data set. Using partial-least squares analysis, the predictive calibration model containing said predictive data set is compared with said second free induction data to predict the concentration of styrene in each of said compositions of K-Resin.

The objects, advantages, and features of the present invention will be apparent from the following description when read in conjunction with the drawings and appended claims.

DETAILED DESCRIPTION

Figure 1:
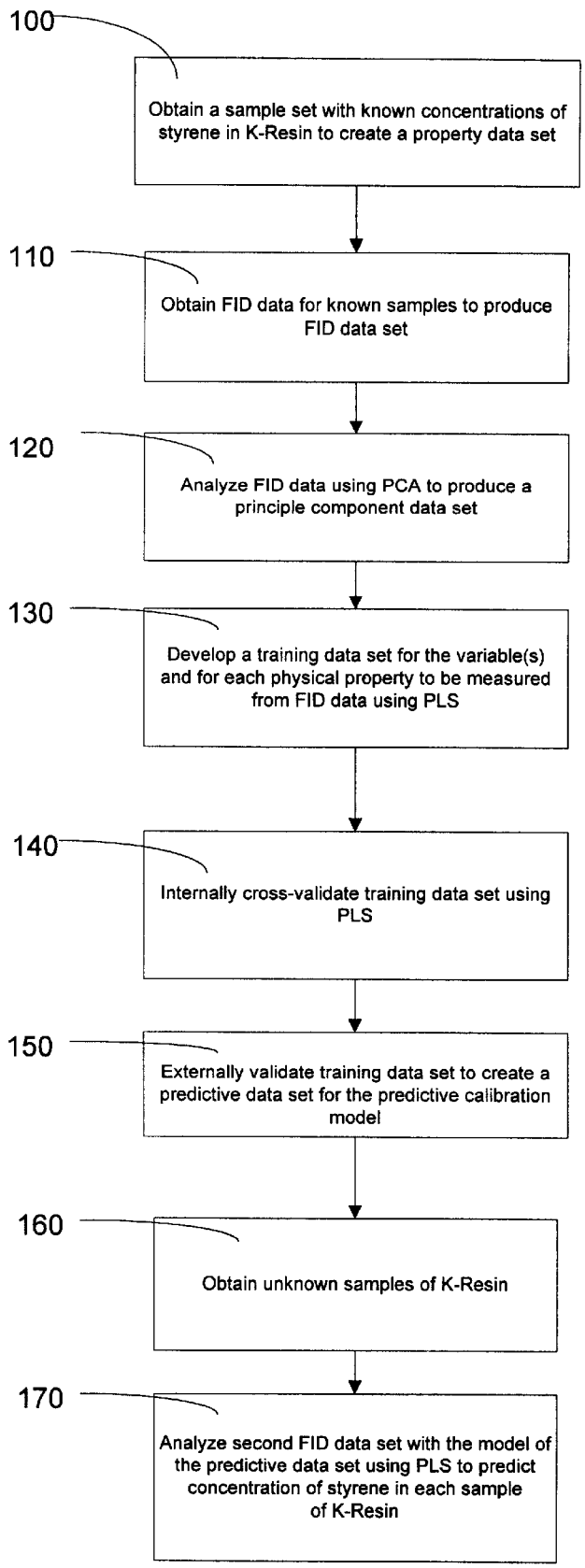
FIG. 1 shows a flowchart of steps performed according to a preferred embodiment of the present invention to determine concentration of styrene in K-Resin.

Determining properties of polymers manually can be very time consuming and often imprecise. Therefore, the present invention employs a chemometric technique for predicting unknown properties of polymers through a predictive model. In a preferred embodiment, a method for prediction of the concentration of styrene in compositions containing homo- and co-polymers of K-Resin is described herein. Referring now to FIG. 1, shown therein is a flow chart of a preferred embodiment of the present invention. Referring to step 100, a first set of samples of homo- and co-polymers of K-Resin is extracted to yield measured concentrations of styrene to create a styrene data set. In a preferred embodiment, replicate samples are collected, preferably collected in triplicate. A precision value is calculated for the triplicate samples to create a predetermined precision value. It should be understood to one skilled in the art that the present invention as disclosed is equally applicable to predict other unknown properties of K-Resin.

Turning now to step 110, each of the samples from the first sample set containing known concentrations of styrene are heated for approximately fifteen minutes in a Thermolyne dry bath heater from about 25° C. to about 55° C. to create a plurality of fluff samples. Each of the plurality of fluff samples are then fed into a probe of a magnet in a nuclear magnetic resonance spectrometer (NMR) such as an Auburn Magmonitor benchtop manufactured by Auburn International, Inc. in Danvers, Mass. In the preferred embodiment, a low resonance NMR which operates at 20 MHz for H-1 frequency provides instrumental analysis of compositions of homo- and co-polymers of K-Resin. A one-pulse sequence as used in a preferred embodiment of the present invention begins the process with the application of a 90 degree pulse of radio frequency followed by a delay of approximately twelve to thirteen microseconds. The receiver gate is then turned on to observe the signal (FID) produced by the 90 degree pulse which is subsequently converted from analog to digital through an analog to digital converter (ADC).

The FID is then sent to a computer such as a Pentium based IBM PC to be used for analysis through a chemometric process. Chemometrics is the chemical discipline that uses mathematical and statistical methods to relate measurements made on a chemical system to the state of the system and to design or select optimal measurement procedures and experiments. In other words, chemometrics is the use of statistical and mathematical techniques to analyze chemical data. A GRAMS 32 software program ("Chemometrics software") from Galactic Inc. is utilized to effectuate the chemometrics techniques of the present invention. The first step in chemometrics is calibration, or the construction of a mathematical model which represents the relationship between the independent variable (e.g. the concentration of xylene soluble polypropylene) and the dependent variables (e.g. the FID curves for polypropylene samples). Since more than one instrument measurement is performed for an individual sample, multivariate calibration must be used. Inverse least squares is the best method for complicated systems in which the properties are not all known since concentrations are treated as a function of the responses as shown in the following equation:

$$c = Rb \tag{Eq. 1}$$

where the (nsamp X 1) vector c contains the concentrations of the samples, R (nsamp X nvars) is a matrix of measurements, and the (nvars X 1) vector b contains the model coefficients. Therefore, a predictive calibration model created through inverse least squares regression techniques can model the relationship between multiple analytes of interest (different c vectors) and the same response matrix (R) using different model coefficients (b vectors). Moreover, using inverse least squares regression, it is possible to predict the concentration of one component even if additional chemical and physical sources of variation are present. Three examples of inverse least squares methods include multiple linear regression ("MLR"), principal component regression ("PCR"), and partial least squares ("PLS") all of which are documented in the following references and are incorporated herein by reference: *Chemometrics*, pp. 281–292 by Muhammad A. Sharaf, Deborah L. Illman, and Bruce R. Kowalski, 1986; and *Chemometrics A Practical Guide*, pp. 245–338 by Kenneth R. Beebe, Randy J. Pell, and Mary Beth Seasholtz, 1998.

When using MLR on data sets found in chemistry, variable selection is often required to make the matrix calculations possible and/or improve the stability of the calculations. It is therefore appropriate to use MLR when the number of variables is small, or in situations where a subset of measurement variables is desired. However, reducing the number of variables will almost always result in poorer error detection ability and less precise estimates.

Unlike MLR, PCR and PLS are methods that can be used without explicitly selecting variables. This is accomplished by transforming the measured variables (e.g., absorbance values at many wavelengths) into new variables (often referred to as factors) that are used in the matrix calculations. The difference between PCR and PLS is in how this variable transformation is performed. Both PCR and PLS have good diagnostic tools and in general the results are similar. These methods are often preferred over MLR unless the number of variables is small or circumstances dictate the explicit reduction in the number of variables. It should be understood to a person skilled in the art that the present invention is adaptable to any inverse least squares method, however in a preferred embodiment, PLS is used.

Turning now to step 120, in a preferred embodiment, principle component analysis ("PCA") is used to analyze all of the points on the FID curves to determine latent variables for a principal component data set. PCA involves mathematical manipulation of a data matrix to represent the variation present in many variables using a small number of principal components (latent variables). A new row space is constructed in which to plot the samples by redefining the axes using principle components rather than the original measurement variables. The new axes, or principal components, allow pattern detection in matrices with many variables using a relatively small number of dimensions.

Therefore, contrary to prior art methods, for purposes of prediction, the PCA method allows all of the variables to be retained in the problem by extracting principle components (latent variables). The latent variables are found by an iterative process and are mutually orthogonal (perpendicular), linear combinations of all the original variables. The latent variables simultaneously describe the maximum predictive variance of a data set in one direction and provide maximal fit to facilitate the creation of a predictive calibration model without limiting the accuracy of the model. Through the use of PCA, outliers can be readily detected and eliminated during predictive calibration modeling as will be described in more detail below.

PCA also allows manipulation of the degree of accuracy desired in the resulting prediction by allowing selection of the specific latent variables to be included in creating the principle component data set. In determining the number of latent variables or principal components to be retained in creating the predictive calibration model, several known in the art techniques such as plots of eigenvalues, ratios of successive eigenvalues, or cross-validation or other similar techniques including combinations of these techniques may be applied. It should be understood that other methods of evaluating clustering of data such as hierarchial cluster analysis (HCA) or any combination thereof are equally applicable to the invention as disclosed in the present invention.

Referring to step 130, creating a predictive calibration model requires utilizing PLS after latent variables from the PCA method are found to correlate the FID data variables to the known quantities. The details of the PLS method can be found in *Chemometrics*, pp. 285–292 by Muhammad A. Sharaf, Deborah L. Illman, and Bruce R. Kowalski, 1986. In a preferred embodiment of the present invention, generally, a single known variable, the concentration of styrene obtained from extraction, comprises one matrix while the digitized data from the FID curves comprise a second matrix. The PLS method contained in the Chemometrics software is then used to correlate the two matrices to find values for the model coefficients to create a training data set. Therefore, no knowledge of the particular equations needed to interpret the FID curve to obtain model coefficients is necessary since PLS uses all of the points of the FID curve during model building. It should be understood to a person skilled in the art that a variety of variables described by individual matrices may be used to create the predictive calibration model using the PLS method.

The training data set is then validated to provide a predictive data set for the predictive calibration model of the present invention as shown in step 140. Validation of the present inventive method occurs in two-fold including an internal as well as an external step. First, the PLS method in the Chemometrics software employs cross-validation in step 140 to internally check the validity of the model. In a preferred embodiment, the Chemometrics software selects and deletes one sample from the first sample set to be left out for prediction and reconstructs a new predictive calibration model from steps 120 through 140 with a new styrene data set, a new free induction decay data set and a new principle component data set. The Chemometrics software then predicts the concentration of styrene for the selected sample left out of the first sample set using the new predictive calibration model. In the preferred embodiment, each of the samples of the first sample set are left out once for prediction with the process of constructing a new predictive calibration model repeated each time. The cross-validation ends with a comparison of the predicted concentration of each of the selected samples of the first sample set with the measured concentration of each of the selected samples of the first sample set, the measured concentration having been obtained during step 110. If the difference between the predicted concentration and the measured concentration is less than the predetermined precision value of the measured concentration, then the Chemometrics software internally validates the training data set. If the difference is higher than the precision value, then a new set of samples are obtained to begin the process at step 100. In another embodiment, a block of samples may be taken to create a block cross validation test to constantly check the accuracy of the model. Through internal validation, PLS and PCA are able to model complex data and identify when the models are no longer valid.

A second validation step as shown in step 150 involves externally validating the training data set created through the Chemometrics software. The external validation is accomplished by obtaining a second sample set of K-Resin with the second sample set comprising a smaller amount of samples than in the first sample set. Then steps 110 through 120 are repeated for each of the samples for the second sample set using a validation styrene data set to yield a validation FID data set. The Chemometrics software then applies the validation FID data set to the training data set to predict the concentration of styrene in each of the samples of the second sample set. Plotting the predicted concentrations of styrene versus the measured concentrations of the styrene yields an $R^2$ value. If the $R^2$ value is above about 0.95, then the training data set is validated to create a predictive calibration model. If the $R^2$ value is below about 0.95, then a new sample set is used to repeat steps 100 through 150 to create a new predictive calibration model. The predicted concentrations can also be used to calculate a relative standard deviation to check the validity of the model.

The prediction, or process of using the model to predict properties of a sample given an instrument output, begins with step 160. Fluff samples of each of the unknown samples of K-Resin are applied to the NMR to produce FID curves for each of the unknown samples, creating a second FID data set as shown in step 160.

The predictive calibration model is then utilized to obtain the concentration of styrene in unknown samples of compositions of K-Resin as shown in step 170. Turning to step 170, the Chemometrics software applies the second FID data set to the predictive calibration model using the PLS method to predict the concentration of styrene in each of the unknown samples of K-Resin.

It should be understood to one skilled in the art that any unknown property of K-Resin may be predicted using the method described in the present invention. Furthermore, the present chemometric method as disclosed allows interpretation of both linear and non-linear properties depicted in the FID curves. Also, unknown properties of both homo- and co-polymers may be predicted with relatively high precision using the present invention. The present invention is also particularly useful in identifying samples that do not fit within a model, thereby indicating a need to develop a new model.

It is clear that the present invention is well adapted to attain the ends and advantages mentioned as well as those inherent therein. While a presently preferred embodiment of the invention has been described for purposes of the disclosure, it will be understood that numerous changes may be made which will readily suggest themselves to those skilled in the art and which are encompassed within the spirit of the invention disclosed and as defined in the appended claims.

That which is claimed is:

1. An on-line process to produce a predictive data set which can be used to predict the concentration of styrene in K-Resin, said process comprising:
    (a) obtaining a first sample set, wherein each sample comprises K-Resin;
    (b) obtaining a measured concentration of styrene for each sample of said first sample set to produce a styrene data set;
    (c) obtaining a free induction decay for each said sample to produce a free induction decay data set;
    (d) analyzing said free induction decay data set using principle component analysis to produce a principle component data set;
    (e) analyzing said styrene data set, said free induction decay data set, and said principle component data set using partial-least squares analysis to produce a training data set; and
    (f) validating said training data set to produce said predictive data set for a predictive calibration model.

2. A process according to claim 1 wherein said validating step (f) is accomplished through internal validation and external validation.

3. A process according to claim 2 wherein said internal validation uses cross-validation comprising the following steps:
    deleting a single sample from said first sample set, thereby creating a new styrene data set;
    analyzing said free induction decay for said new styrene data set using principle component analysis to produce a new free induction decay data set and a new principle component data set;
    analyzing said new styrene data set, said new free induction decay data set, and said new principle component data set using partial-least squares analysis to produce a new training data set; and
    applying said deleted sample to said new training data set to predict a predicted concentration of styrene;
    determining a difference between said predicted concentration and said measured concentration of said deleted sample;
    completing internal validation when said difference is less than a predetermined precision value; and
    repeating steps (a) through (f) if said difference is greater than said predetermined precision value.

4. A process according to claim 3 wherein said external validation comprises the steps of:
    obtaining a second sample set of said K-Resin wherein said second sample set comprises fewer samples than said first sample set;
    obtaining a measured concentration of styrene for each sample of said second sample set to produce a validation styrene data set;
    obtaining a free induction decay for each said sample to produce a validation free induction decay data set;
    applying said validation free induction decay data set to said training data set to predict a predicted concentration of styrene for each sample of said second sample set;
    determining an $R^2$ value for said predicted amounts;
    validating said training data set if said $R^2$ value is above about 0.95; and
    repeating steps (a) through (f) if said $R^2$ value is less than about 0.95.

5. A process according to claim 4 wherein said free induction decay data set comprises a plurality of data points.

6. A process according to claim 5 wherein said measured concentration of styrene obtained in step (b) is obtained through extraction.

7. A process according to claim 6 further comprising a step of:
    (g) heating each said composition before step (c) to a temperature of from about 25° C. to about 55° C.

8. A process according to claim 7 wherein all said plurality of data points of said free induction decay data set are used in step (d) as variables for said principle component analysis and wherein latent variables are determined for creating said principle component data set.

9. A process according to claim 8 wherein a low resolution H-1 NMR is used in step (c).

10. An on-line process of using a predictive data set to predict the concentration of styrene in K-Resin, said process comprising:
    (a) obtaining an unknown sample set, wherein each unknown sample comprises K-Resin;
    (b) obtaining a free induction decay for each said unknown sample to produce a free induction decay data set containing a plurality of data points; and
    (c) applying said free induction decay data set to said predictive data set using partial-least squares analysis to predict a concentration of styrene in each said unknown sample of K-Resin.

11. A process according to claim 10 further comprising a step of:
    (d) heating each said composition before step (b) to a temperature of from about 25° C. to about 55° C.

12. A process according to claim 11 wherein a low resolution H-1 NMR is used in step (b).

13. An on-line process to predict the concentration of xylene soluble polypropylene in a composition, said process comprising:
    (a) producing a predictive data set, said predictive data set generated by:
        (a1) obtaining a first sample set, wherein each sample comprises K-Resin;
        (a2) obtaining a measured concentration of styrene for each sample of said first sample set to produce a styrene data set;
        (a3) obtaining a free induction decay for each said sample to produce a free induction decay data set;
        (a4) analyzing said free induction decay data set using principle component analysis to produce a principle component data set;
        (a5) analyzing said styrene data set, said free induction decay data set, and said principle component data set using partial-least squares analysis to produce a training data set;
        (a6) validating said training data set to produce said predictive data set;
    (b) using said predictive data set to predict the concentration of styrene, said concentration predicted by:
        (b1) obtaining an unknown sample set, wherein each unknown sample in said unknown sample set contains K-Resin;
        (b2) obtaining a free induction decay for each said unknown sample to produce a second free induction decay data set; and
        (b3) applying said second free induction decay data set to said predictive data set using partial-least squares analysis to predict a concentration of styrene in each said sample.

14. A process according to claim 13 wherein the concentration of styrene obtained in step (a2) is obtained through extraction.

15. A process according to claim 13 further comprises a step of:
   (a7) heating each said composition before step (a3) to a temperature of from about 25° C. to about 55° C.

16. A process according to claim 13 wherein a low resolution H-1 NMR is used in step (a3).

17. A process according to claim 13 wherein said second free induction decay data set comprises a plurality of data points.

18. A process according to claim 17 wherein all said plurality of data points of said free induction decay data set are used in step (a4) as variables for said principal component analysis and wherein latent variables are determined in step (a4) for creating said principle component data set.

19. A process according to claim 17 wherein said validating step (a6) is accomplished through internal cross-validation followed by external validation.

20. A process according to claim 19 wherein said internal validation uses cross-validation comprising the following steps:
   deleting a single sample from said first sample set, thereby creating a new styrene data set;
   analyzing said free induction decay for said new styrene data set using principle component analysis to produce a new free induction decay data set and a new principle component data set;
   analyzing said new xylene soluble polypropylene data set, said new free induction decay data set, and said new principle component data set using partial-least squares analysis to produce a new training data set; and
   applying said deleted sample to said new training data set to predict a predicted concentration of styrene in said deleted sample;
   determining a difference between said predicted concentration and said measured concentration of said deleted sample;
   completing internal validation when said difference is less than a predetermined precision value; and
   repeating steps (a1) through (a6) if said difference is greater than said predetermined precision value.

21. A process according to claim 20 wherein said external validation comprises the steps of:
   obtaining a second sample set of K-Resin wherein said second sample set comprises fewer samples than said first sample set;
   obtaining a measured concentration of styrene for each sample of said second sample set to produce a validation styrene data set;
   obtaining a free induction decay for each said sample to produce a validation free induction decay data set;
   applying said validation free induction decay data set to said training data set to predict a predicted concentration of styrene for each sample of said second sample set;
   determining an $R^2$ value for said predicted concentrations;
   validating said training data set if said $R^2$ value is above about 0.95; and
   repeating steps (a1) through (a6) if said $R^2$ value is less than about 0.95.

* * * * *